(12) United States Patent
Isogimi

(10) Patent No.: US 7,465,310 B2
(45) Date of Patent: *Dec. 16, 2008

(54) MEDICAL KNIFE

(75) Inventor: Kazuhiko Isogimi, Seki (JP)

(73) Assignee: Kai & R&D Center Co., Ltd., Gifu-ken (JP)

( * ) Notice: Subject to any disclaimer, the term of this patent is extended or adjusted under 35 U.S.C. 154(b) by 413 days.

This patent is subject to a terminal disclaimer.

(21) Appl. No.: 10/952,855

(22) Filed: Sep. 30, 2004

(65) Prior Publication Data

US 2005/0070941 A1    Mar. 31, 2005

(30) Foreign Application Priority Data

Sep. 30, 2003    (JP) .............................. 2003-341599

(51) Int. Cl.
*A61B 17/32*    (2006.01)
(52) U.S. Cl. .................................................. 606/167
(58) Field of Classification Search ................. 606/166, 606/167, 107; 623/6.12
See application file for complete search history.

(56) References Cited

U.S. PATENT DOCUMENTS

| | | | |
|---|---|---|---|
| 5,002,565 A * | 3/1991 | McGregor ................ | 606/223 |
| 6,139,559 A * | 10/2000 | Nordan et al. ............. | 606/166 |
| RE37,304 E | 7/2001 | Van Heugten et al. | |
| 6,547,802 B1 * | 4/2003 | Nallakrishnan et al. ..... | 606/166 |
| 6,554,840 B2 | 4/2003 | Matsutani et al. | |
| D535,747 S * | 1/2007 | Isogimi .................... | D24/146 |
| 2001/0029386 A1 * | 10/2001 | Matsutani et al. ........... | 606/166 |

FOREIGN PATENT DOCUMENTS

| | | |
|---|---|---|
| JP | A-H09-276284 | 10/1997 |
| JP | A-2001-238890 | 9/2001 |
| JP | B2-H06-20461 | 3/2004 |

* cited by examiner

Primary Examiner—(Jackie) Tan-Uyen T Ho
Assistant Examiner—Melanie Tyson
(74) Attorney, Agent, or Firm—Posz Law Group, PLC

(57) ABSTRACT

A section of a first side of a blade between a cutting edge and a boundary line forms a cutting surface. An angle of a section of the cutting surface in the vicinity of the boundary line with respect to a hypothetical plane extending from the cutting edge and defined between the first and second sides of the blade is larger than an angle of a section of the cutting surface in the vicinity of the cutting edge with respect to the hypothetical plane. Therefore, the medical knife has an improved configuration such that the cutting performance of the knife is improved.

12 Claims, 14 Drawing Sheets

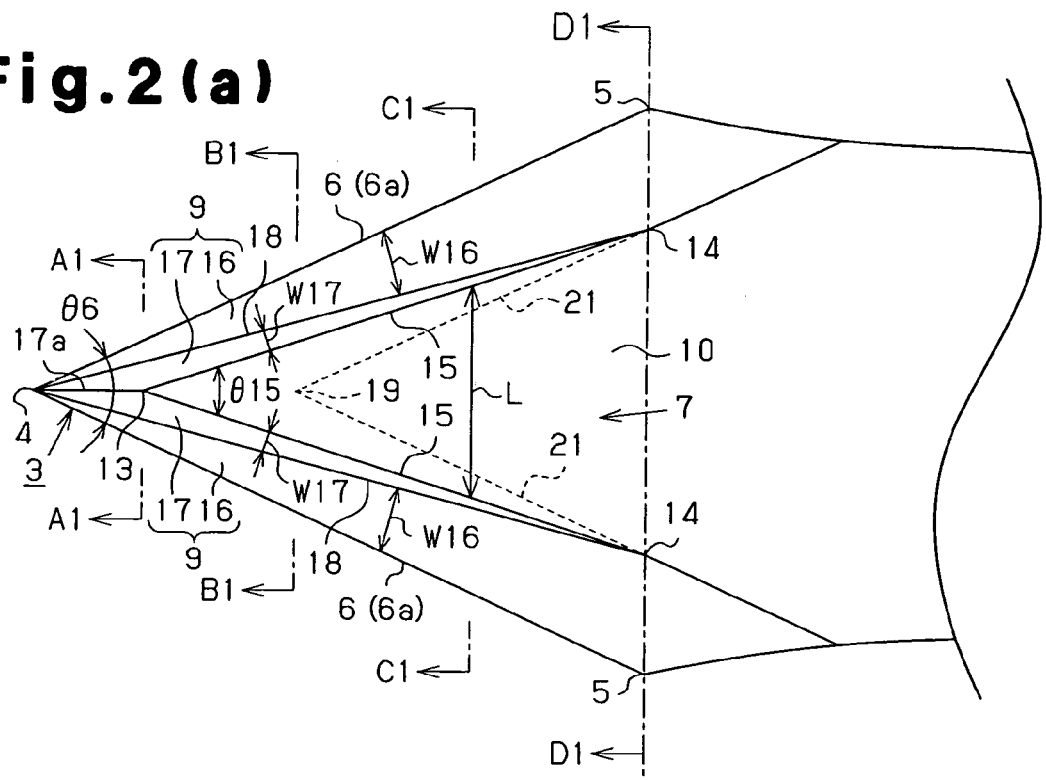
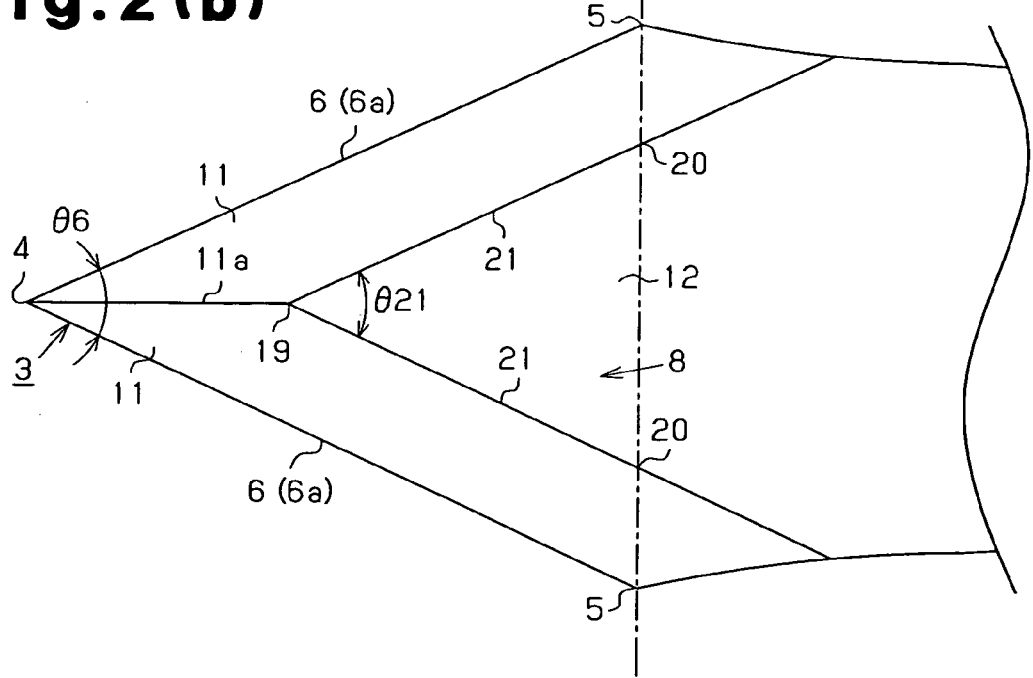

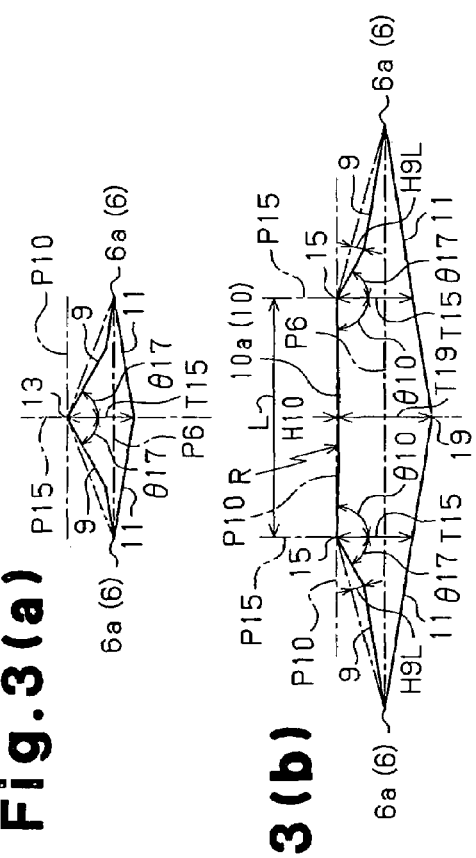
Fig.3(a)
Fig.3(b)
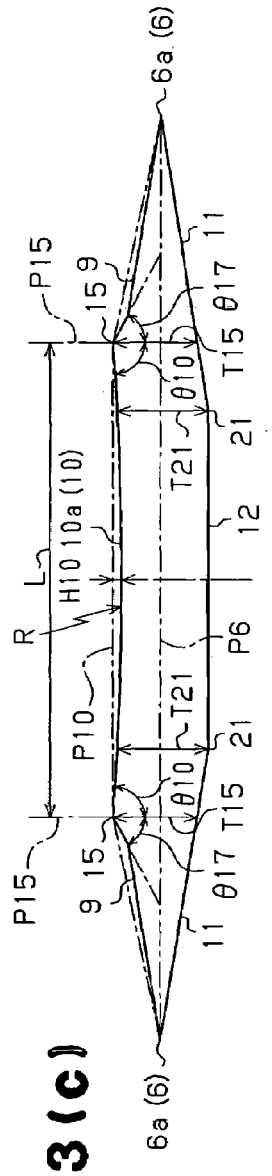
Fig.3(c)
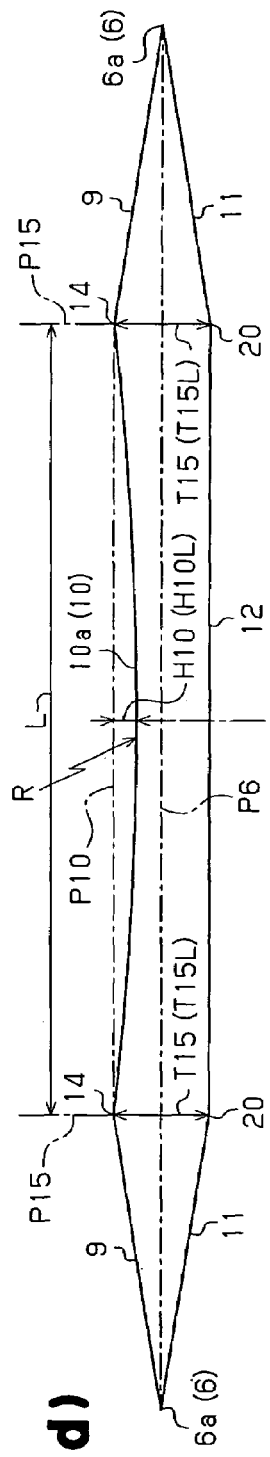
Fig.3(d)

MEDICAL KNIFE

BACKGROUND OF THE INVENTION

The present invention relates to medical knifes used in surgeries for cutting biological tissue such as eye tissue.

FIGS. 14 and 15 each show a conventional medical knife described in Japanese Laid-Open Patent Publication No. 2001-238890. The medical knife includes a pair of first cutting surfaces and a first intermediate surface 106c formed at a first side 106 of a blade 101. In each first cutting surface, an outer slanted surface 106a and an inner slanted surface 106b are defined. A hypothetical plane 105 extends between a pair of cutting edges 103 of the blade 101. The angle between the hypothetical plane 105 and each of the inner slanted surfaces 106b, that is a semi cutting angle of the inner slanted surface 106b, is smaller than the angle between the hypothetical plane 105 and each of the outer slanted surfaces 106a, that is a semi cutting angle of the outer slanted surface 106a.

Also, a pair of opposed second cutting surfaces are formed at a second side 107 of the blade 101. In each second cutting surface, a slanted surface 107a is defined between the cutting edge 103 and the contour line 107c. The angle between each slanted surface 107a and the hypothetical plane 105, that is a semi cutting angle of the slanted surface 107a, is uniform. A planar surface 107b extends between the contour lines 107c and parallel with the hypothetical plane 105.

Thus, if the cutting edges 103 are formed relatively sharp, the thickness between the first side 106 and the second side 107 of the blade 101 becomes relatively small, seconding the strength of the blade 101. However, if the thickness between the first side 106 and the second side 107 is maintained at a relatively large value for saving the strength of the blade 101, the sharpness of each of the cutting edges 103 becomes insufficient. This limits the cutting performance of the medical knife.

SUMMARY OF THE INVENTION

Accordingly, it is an objective of the present invention to provide a medical knife having an improved configuration such that the cutting performance of the knife is improved.

To achieve the foregoing and other objectives and in accordance with the purpose of the present invention, the invention provides a medical knife having a blade. The blade includes a distal end and a proximal end. A pair of opposed, first and second sides extend from the distal end to the proximal end. A cutting edge is formed between the first and second sides and extending from the distal end to the proximal end. A boundary line is defined on the first side and extending from the distal end to the proximal end. A section of the first side between the cutting edge and the boundary line forms a cutting surface. An angle of a section of the cutting surface in the vicinity of the boundary line with respect to a hypothetical plane extending from the cutting edge and defined between the first and second sides is larger than an angle of a section of the cutting surface in the vicinity of the cutting edge with respect to the hypothetical plane.

Another aspect of the present invention provides a medical knife having a blade the cutting surface of which has a recessed surface with respect to a hypothetical plane extending between a cutting edge and a boundary line.

Other aspects and advantages of the invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which:

FIG. 2(a) is an enlarged view showing a portion of a front side of a blade;

FIG. 2(b) is an enlarged view showing a portion of a rear side of a blade;

FIG. 3(a) is an enlarged cross-sectional view taken along line A1-A1 of FIG. 2(a);

FIG. 3(b) is an enlarged cross-sectional view taken along line B1-B1 of FIG. 2(a);

FIG. 3(c) is an enlarged cross-sectional view taken along line C1-C1 of FIG. 2(a);

FIG. 3(d) is an enlarged cross-sectional view taken along line D1-D1 of FIG. 2(a);

DETAILED DESCRIPTION OF THE PREFERRED EMBODIMENTS

Figure 1:
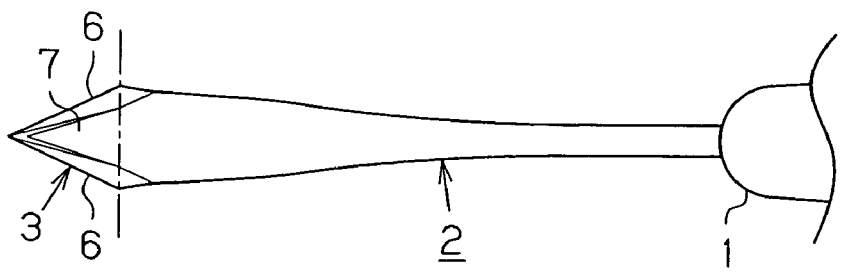
FIG. 1(a) is an elevation view showing a medical knife according to a first embodiment of the present invention.
FIG. 1(b) is an enlarged front view showing a portion of FIG. 1(a)
FIG. 1(c) is an enlarged rear view showing a portion of FIG. 1(a)
Figure 1:
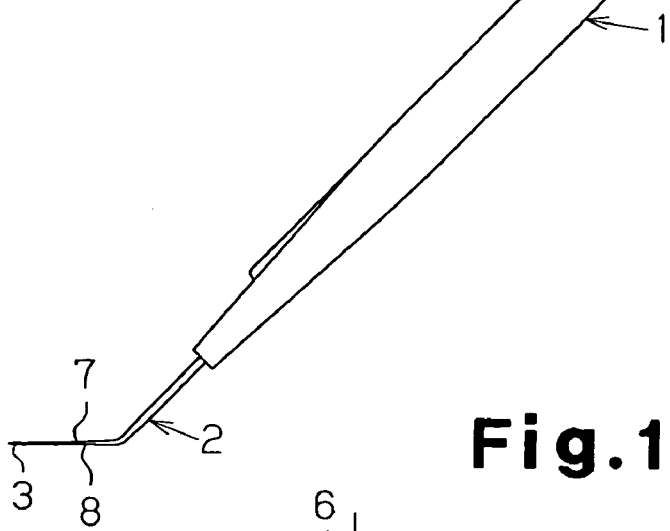
Figure 1:
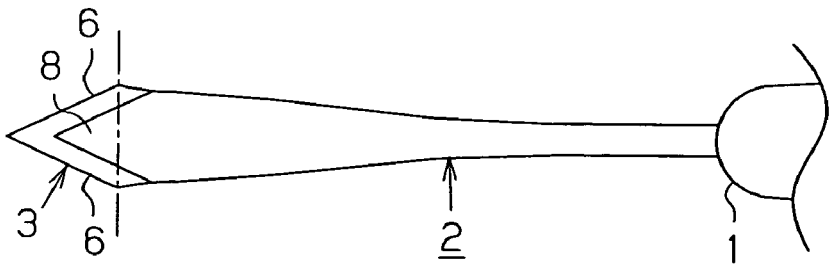
Figure 4A:
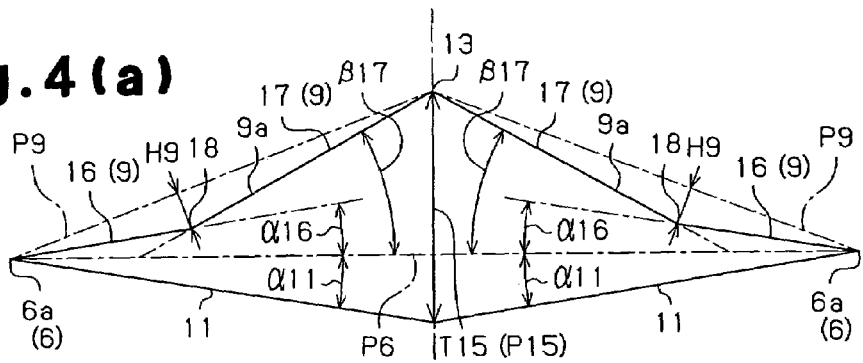
FIGS. 4(a) to 4(d) are enlarged views showing a portion of FIGS. 3(a) to 3(d), respectively.
Figure 4B:
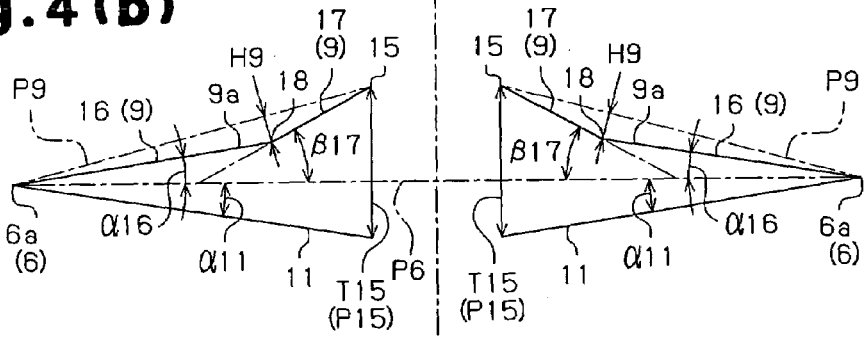
Figure 4C:
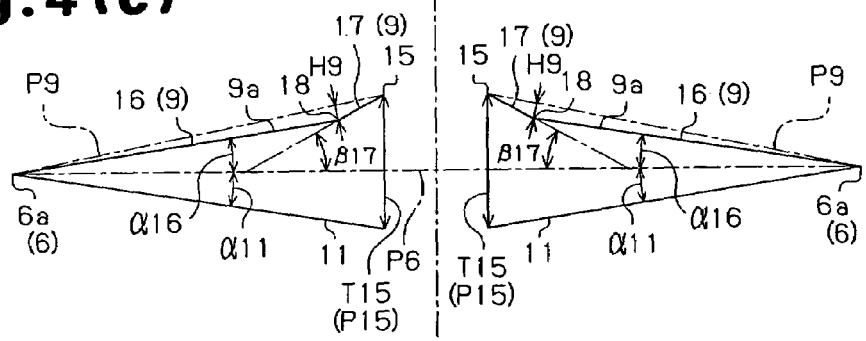
Figure 4D:
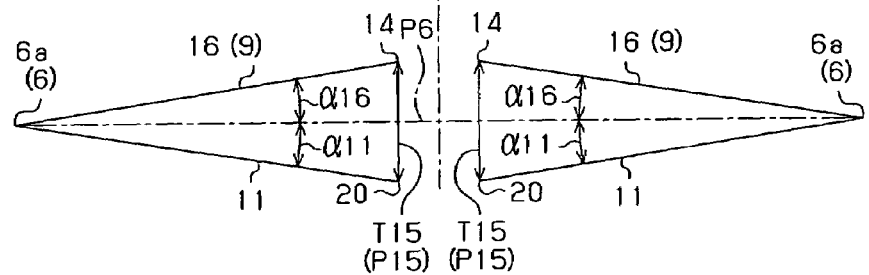
Figure 5A:
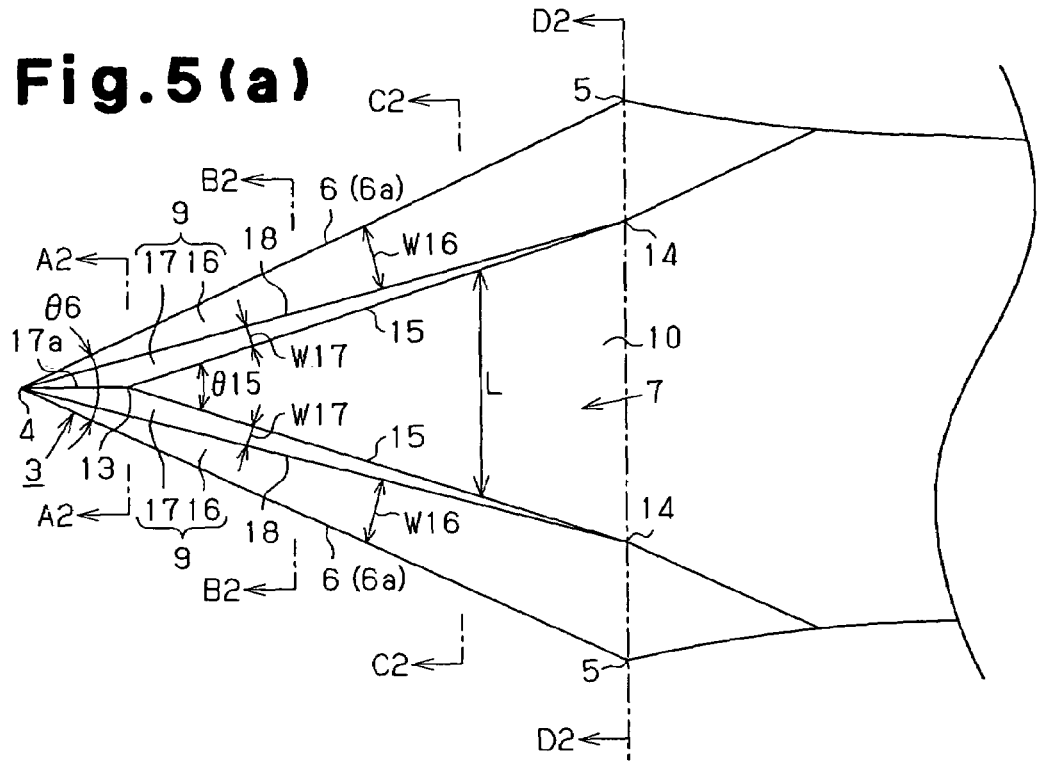
FIG. 5(a) is an enlarged view showing a portion of a front side of a blade according to a second embodiment of the present invention.
Figure 5B:
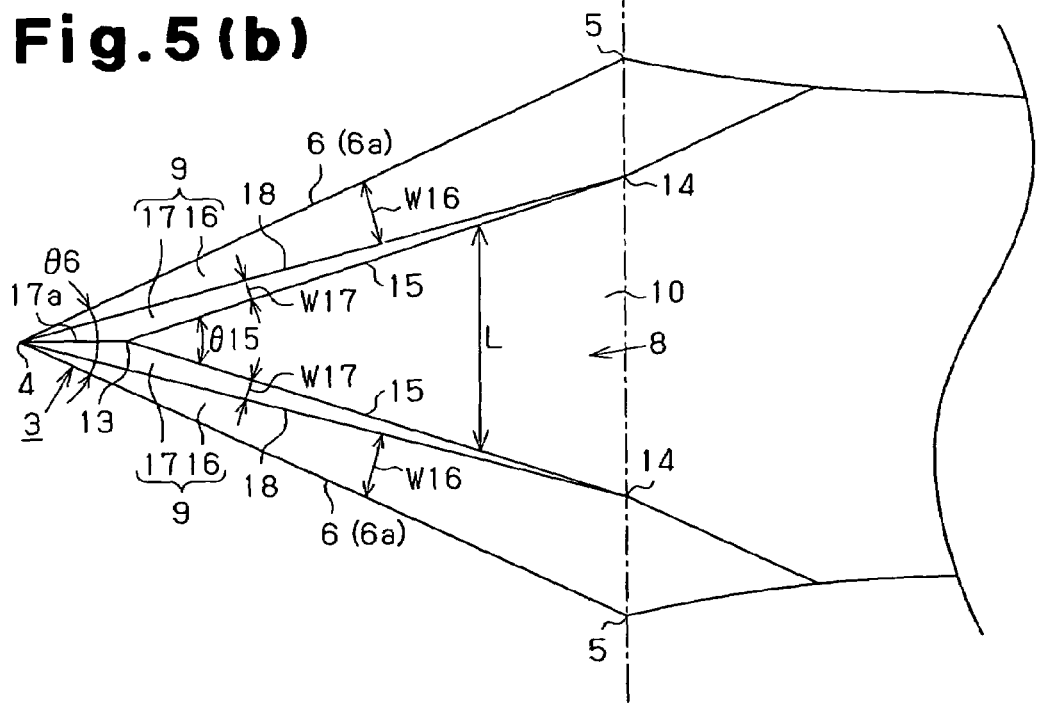
FIG. 5(b) is an enlarged view showing a portion of a rear side of the blade of FIG. 5(a)
Figure 6A:
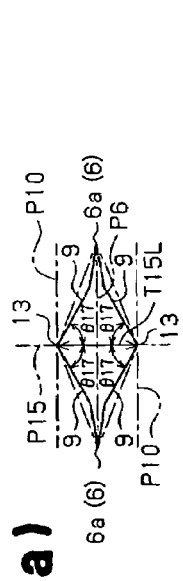
FIGS. 6(a) to 6(d) are enlarged cross-sectional views taken along line A2-A2, B2-B2, C2-C2, and D2-D2 of FIG. 5(a), respectively.
Figure 6B:
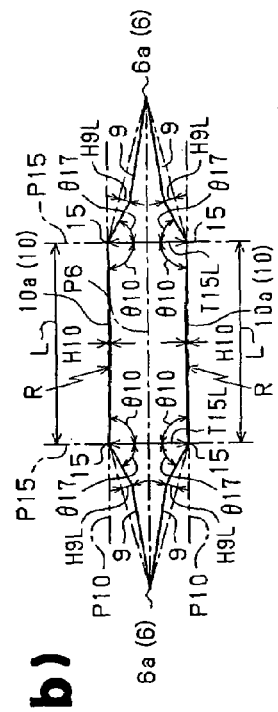
Figure 6C:
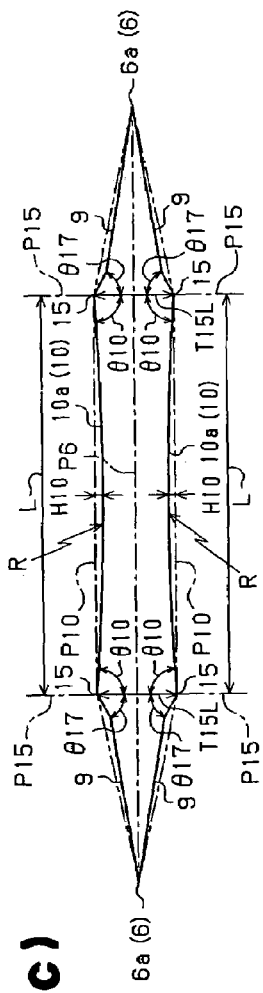
Figure 6D:
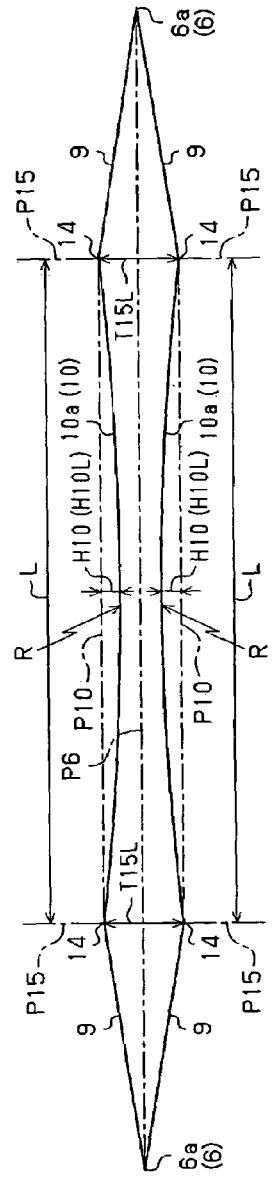
Figure 7A:
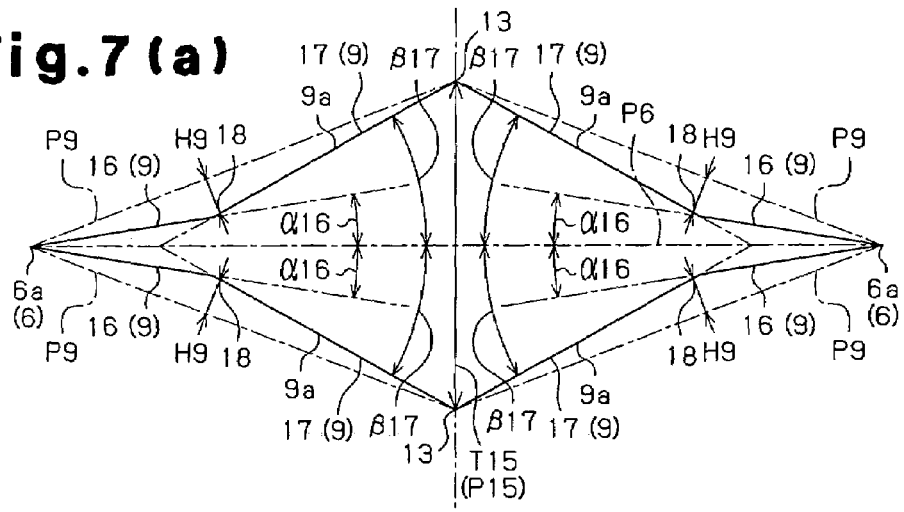
FIGS. 7(a) to 7(d) are enlarged views showing a portion of FIGS. 6(a) to 6(d), respectively.
Figure 7B:
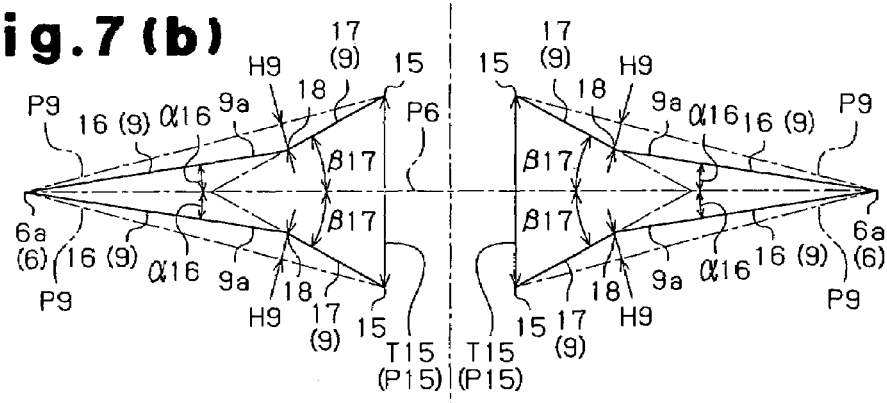
Figure 7C:
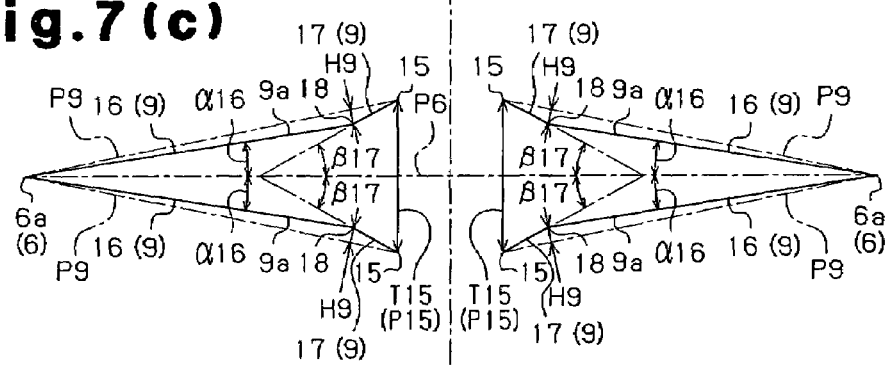
Figure 7D:
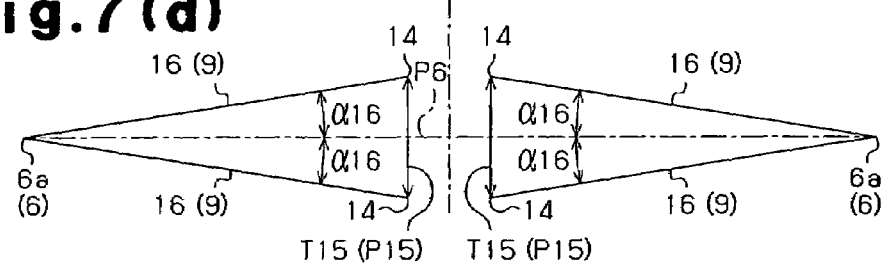
Figure 8A:
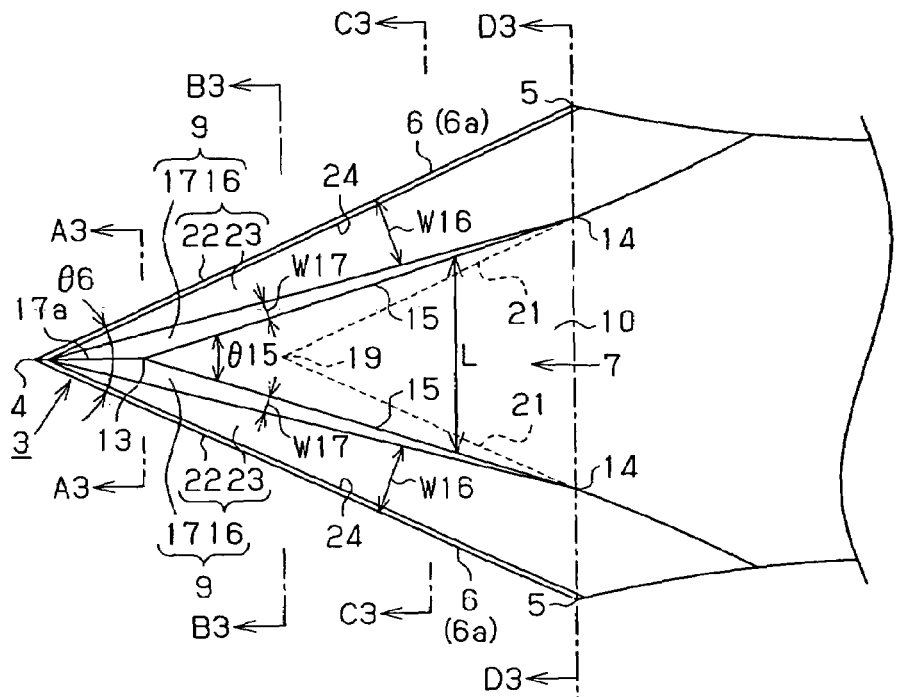
FIG. 8(a) is an enlarged view showing a portion of a front side of a blade according to a third embodiment of the present invention.
Figure 8B:
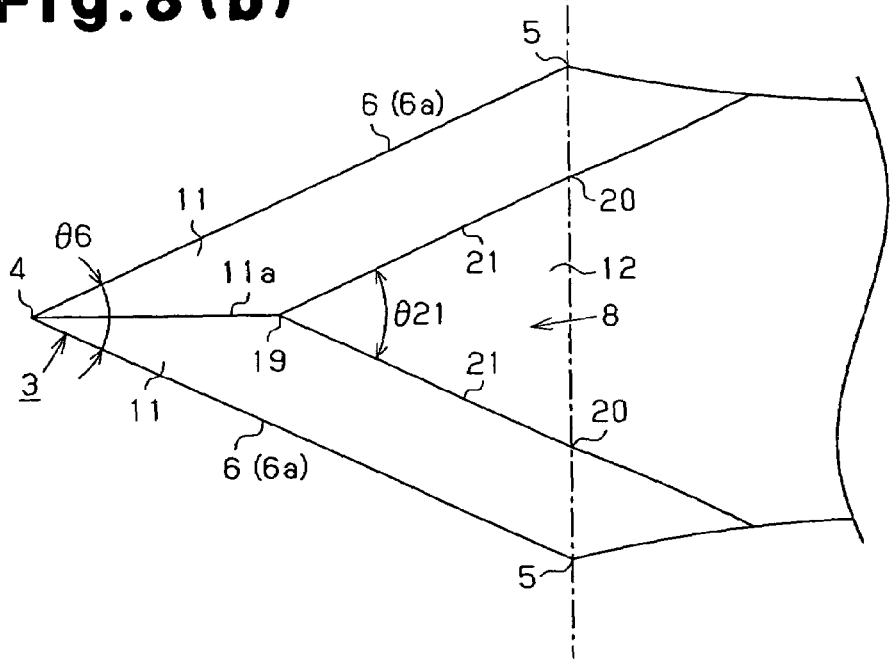
FIG. 8(b) is an enlarged view showing a portion of a rear side of the blade of FIG. 8(a)
Figure 9A:
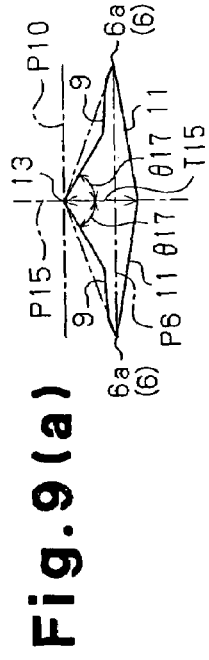
FIGS. 9(a) to 9(d) are enlarged cross-sectional views taken along line A3-A3, B3-B3, C3-C3, and D3-D3 of FIG. 8(a), respectively.
Figure 9B:
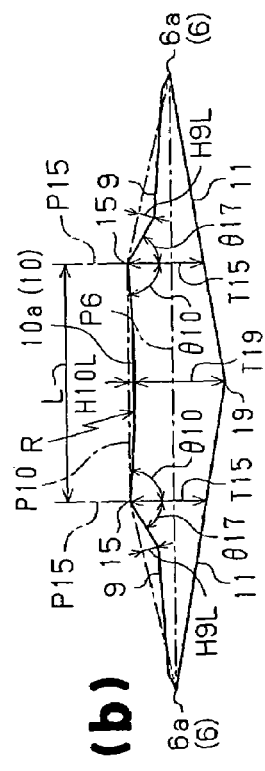
Figure 9C:
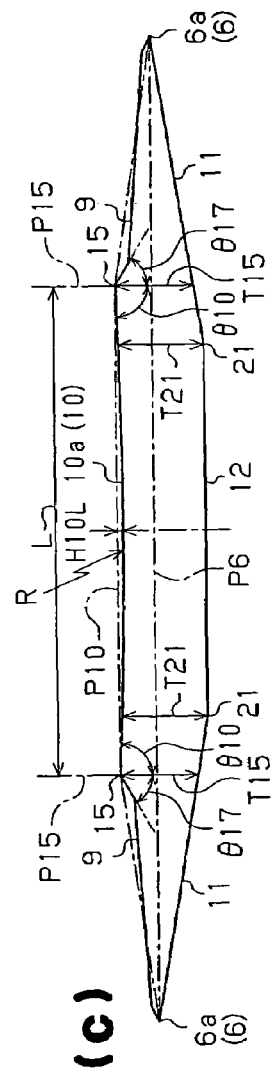
Figure 9D:
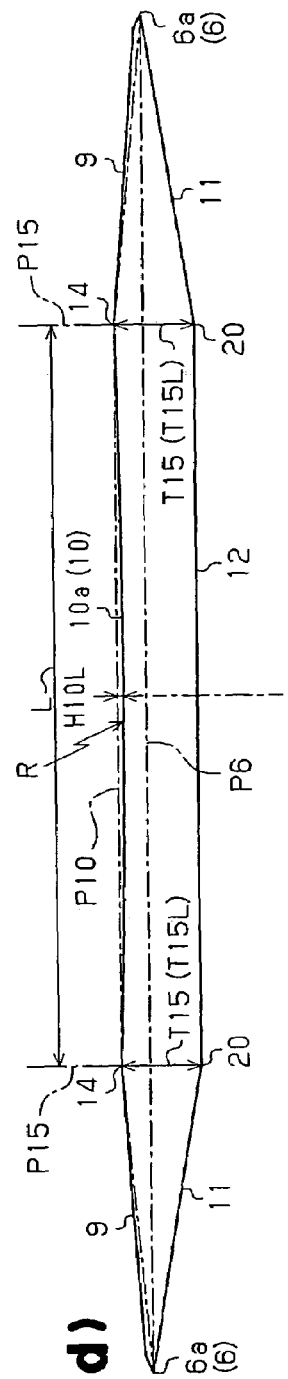
Figure 10A:
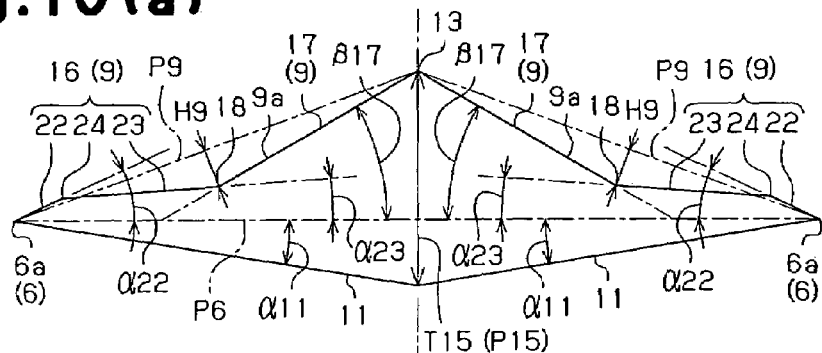
FIGS. 10(a) to 10(d) are enlarged views showing a portion of FIGS. 9(a) to 9(d), respectively.
Figure 10B:
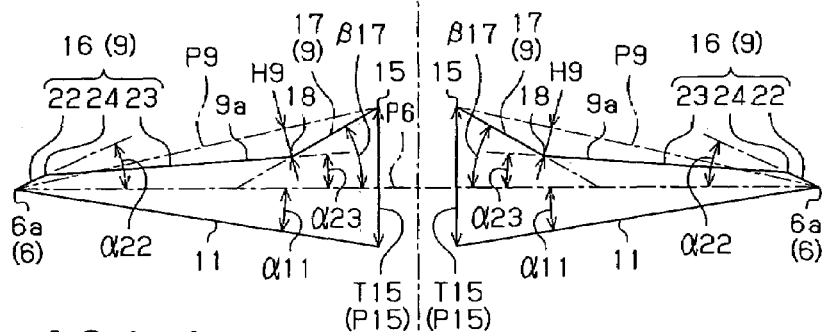
Figure 10C:
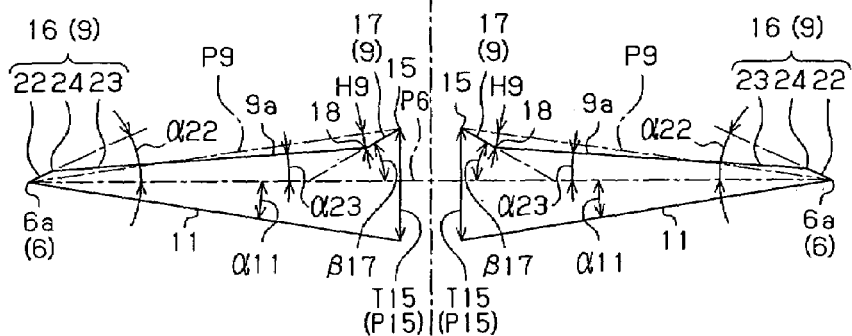
Figure 10D:
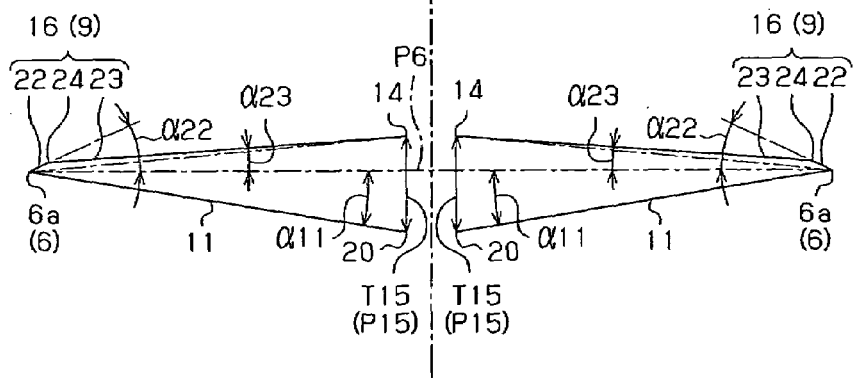

A medical knife according to a first embodiment of the present invention will be described with reference to FIGS. 1(a) to 4(d).

As illustrated in FIGS. 1(a) to 1(c), the medical knife is used surgically for dissecting eye tissue and includes a synthetic resin handle 1 and a metal plate 2. The plate 2 is attached to the handle 1 and is bent. A blade 3 is formed at a distal end of the plate 2. The plate 2 includes a front side 7 (a first side) and a rear side 8 (a second side). As shown in FIGS. 2(a) and 2(b), the front side 7 and the rear side 8 are defined between a pair of outer end lines 6 in an opposing manner. Each of the outer end lines 6 extends from a cutting point 4 (the distal end) to a corresponding one of proximal ends 5. A cutting edge 6a is formed along the entire portion of each outer end line 6. An angle θ6 defined by the opposing outer end lines 6 with respect to the cutting point 4 at each of the sides 7, 8 is not less than 15 degrees but not more than 120 degrees. With reference to FIG. 2(a), the front side 7 of the blade 3 includes a pair of first cutting surfaces 9 opposed to each other. Each of the first cutting surfaces 9 includes a corresponding one of the cutting edges 6a. An intermediate surface 10 extends between the opposing first cutting surfaces 9. Likewise, with reference to FIG. 2(b), the rear side 8 of the blade 3 includes a pair of second cutting surfaces 11 opposed to each other. Each of the second cutting surfaces 11 includes a corresponding one of the cutting edges 6a. A second intermediate surface 12 extends between the opposing second cutting surfaces 11.

The first intermediate surface 10 corresponds to a triangular zone connecting a distal end 13 to each of the proximal ends 14. A boundary, inner end line 15 is defined between each of the first cutting surfaces 9 and the first intermediate surface 10 and opposed to a corresponding one of the cutting edges 6a. Each of the inner end lines 15 extends from the distal end 13 of the first intermediate surface 10 to a corresponding one of the proximal ends 14. Each first cutting surface 9 is formed by an outer cutting surface 16 including the corresponding-cutting edge 6a and an inner cutting surface 17 defined between the outer cutting surface 16 and the first intermediate surface 10. Each of the outer cutting surfaces 16 and the associated inner cutting surface 17 are located between the corresponding cutting edge 6a and the associated inner end line 15.

Each of a pair of concave lines 18 extends from the cutting point 4 of the cutting edges 6a to the proximal end 14 of the corresponding inner end line 15 of the first intermediate surface 10 and between the corresponding cutting edge 6a and the inner end line 15. Each outer cutting surface 16 is separated from the associated inner cutting surface 17 by the corresponding one of the concave lines 18. The outer cutting surfaces 16 and the inner cutting surface 17 extend along the corresponding cutting edge 6a and the associated inner end line 15. Each of the outer cutting surfaces 16 of the front side 7 is formed by a triangular zone interconnecting the proximal end 14 of the corresponding inner end line 15, the cutting point 4 of the cutting edges 6a, and the proximal end 5 of the corresponding cutting edge 6a. A width W16 of each outer cutting surface 16 between the corresponding cutting edge 6a and the associated inner cutting surface 17 gradually increases from the distal end 4 toward the proximal end 5.

Each of the inner cutting surfaces 17 of the front side 7 is formed by a triangular zone interconnecting the distal end 13 of the inner end lines 15, the proximal end 14 of the corresponding inner end line 15, and the cutting point 4 of the cutting edges 6a. A width W17 of each inner cutting surface 17 between the corresponding outer cutting surfaces 16 and the first intermediate surface 10 gradually decreases from the distal end 13 toward the corresponding proximal end 14 of the first intermediate surface 10. The inner cutting surfaces 17 are connected to each other by a connecting portion 17a connecting the cutting point 4 of the cutting edges 6a to the distal end 13 of the first intermediate surface 10. An angle θ15 defined by the inner end lines 15 with respect to the distal end 13 of the first intermediate surface 10 is not less than 15 degrees but not more than 120 degrees.

With reference to each of the cross sectional views taken along lines A1-A1, B1-B1, C1-C1, and D1-D1 of FIG. 2(a), or FIGS. 3(a) to 3(d), the intermediate surface 10 of the front side 7 defines a recess 10a recessed with respect to a hypothetical plane P10 extending between the inner end lines 15. The recess 10a is defined by a continuous arched surface including the inner end lines 15 and extending between and along the inner end lines 15. The recessed amount of the recess 10a gradually increases from each of the inner end lines 15 toward an intermediate portion between the inner end lines 15. In other words, the recessed amount of the recess 10a is maximum at the intermediate portion between the inner end lines 15. The radius of curvature R of the recess 10a is not less than 5 millimeters but not more than 50 millimeters. Preferably, the radius of curvature R is not less than 10 millimeters but not more than 25 millimeters.

A width L of the intermediate surface 10 gradually increases from the distal end 13 toward the proximal ends 14 of the inner end lines 15. The recessed amount of the recess 10a also increases in this manner. A hypothetical plane P6 extends between the outer end lines 6. A plane extending perpendicular to the hypothetical plane P6 and including the inner end lines 15 is defined as a hypothetical plane P15. A thickness T15 is defined between the front side 7 and the rear side 8 along the plane P15. A thickness T19 is defined between the front side 7 and the rear side 8 along a hypothetical line including a distal end 19 of an inner end line 21 of the rear side 8, which will be described later, and extending perpendicular to the hypothetical plane. A thickness T21 is defined between the front side 7 and the rear side 8 along a hypothetical line including an inner end line 21, which will be described later, and extending perpendicular to the hypothetical plane P6.

Among the thicknesses T15, T19, and T21, a maximal thickness is indicated by index T15L. Regarding the recessed amount H10 of the recess 10a defined with respect to the hypothetical plane P10, a maximum recessed amount (corresponding to the maximally recessed portion of the recess 10a) is indicated by index H10L. The ratio of the maximum recessed amount H10L with respect to the maximum thickness T15L (H10L/T15L) is not less than 0.05 but not more than 0.5, and, preferably, not less than 0.1 but not more than 0.3. Further, the maximum thickness T15L is not less than 0.05 millimeters but not more than 3.0 millimeters, and, preferably, not less than 0.1 millimeters but not more than 0.5 millimeters.

An angle θ10 is defined between the first intermediate surface 10 and the hypothetical plane P15. An angle θ17 is defined between each inner cutting surface 17 and the corresponding hypothetical plane P15. The angle θ10 is larger than the angle θ17.

The second intermediate surface 12 is formed by a triangular zone connecting a distal end 19 and a pair of proximal ends 20. A boundary, inner end line 21 is defined between each of the second cutting surfaces 11 and the second intermediate surface 12. Each of the inner end lines 21 extends parallel with the corresponding cutting edge 6a from the distal end 19 to the corresponding proximal end 20. Each second cutting surface 11 is formed by a zone interconnecting the cutting point 4 of the cutting edges 6a, the proximal end of the corresponding cutting edge 6a, the corresponding proximal end 20 of the inner end lines 21, and the distal end 19 of the inner end lines 21. The second cutting surfaces 11 are connected to each other by a boundary portion 11a connecting the cutting point 4 to the distal end 19 of the inner end line 21. An angle θ21 defined by the inner end lines 21 with respect to the distal end 19 of the inner end lines 21 is not less than 15 degrees but not more than 120 degrees. The second intermediate surface 12 is formed as a plane extending between the inner end lines 21, each of which forms a boundary with respect to the corresponding second cutting surface 11. However, like the first intermediate surface 10 with the recess 10a, the second intermediate surface 12 may be formed as a recess.

With reference to FIGS. 4(a) to 4(d), a semi cutting angle α16 is defined between the outer cutting surface 16 of each first cutting surface 9 and the hypothetical plane P6, which extends between the cutting edges 6a. Similarly, a semi cutting angle β17 is defined between the inner cutting surface 17 of each first cutting surface 9 and the hypothetical plane P6. The semi cutting angle β17 of each inner cutting surface 17 is larger than the semi cutting angle α16 of each outer cutting surface 16. Further, a semi cutting angle α11 is defined between each second cutting surface 11 and the hypothetical plane P6. A full cutting angle (β17+α11) is thus defined between the inner cutting surface 17 of each first cutting surface 9 and the corresponding second cutting surface 11. Likewise, a full cutting angle (α16+α11) is defined between the outer cutting surface 16 of each first cutting surface 9 and the corresponding second cutting surface 11. The full cutting angle (β17+α11) is larger than the full cutting angle (α16+α11). The angle α16 is not less than 5 degrees but not more than 30 degrees. The angle β17 is not less than 10 degrees but not more than 60 degrees. The angle α11 is not less than zero degree but not more than 45 degrees. More preferably, the angle β17 is not less than 20 degrees but not more than 40 degrees.

Each first cutting surface 9 has a recess 9a recessed with respect to a hypothetical plane P9 extending between the corresponding cutting edge 6a and the inner end line 15 of the associated inner cutting surface 17. The recess 9a is defined by each of the outer cutting surface 16 and the corresponding inner cutting surface 17. The concave line 18 between the outer cutting surface 16 and the inner cutting surface 17 corresponds to a maximally recessed portion of the recess 9a with respect to the hypothetical plane P9. In FIGS. 3(a) to 3(d), a maximum value of the thickness T15 is indicated by index T15L. Further, a maximum value of the recessed amount H9 of the recess 9a of each first cutting surface 9 with respect to the hypothetical plane P9 is indicated by index H9L (corresponding to the maximally recessed portion). The ratio between the two values (H9L/T15L) is not less than 0.05 but not more than 0.5, or, preferably, not less than 0.1 but not more than 0.3.

The outer cutting surface 16 and the inner cutting surface 17 of each first cutting surface 9 may be inclined such that the distance between the outer cutting surface 16 or the inner cutting surface 17 and the hypothetical plane P6 gradually increases from the corresponding cutting edge 6a to the associated inner end line 15 (the semi cutting angles α16, β17 are positive). However, the outer cutting surface 16 and the inner cutting surface 17 may be inclined such that the aforementioned distance gradually decreases from the corresponding cutting edge 6a to the associated inner end line 15 (the semi cutting angles α16, β17 are negative). Alternatively, the outer cutting surface 16 and the inner cutting surface 17 may be shaped such that the distance becomes constant from the corresponding cutting edge 6a to the associated inner end line 15 (the semi cutting angles α16, β17 are null). In the first embodiment and the remaining, second to fourth embodiments, which will be described later, the outer cutting surface 16 and the inner cutting surface 17 of each first cutting surface 9 are shaped such that the cutting angle (the semi cutting angles α16, β17) becomes positive.

The first embodiment has the following effects.

(1) In the medical knife of this embodiment, each of the outer end lines 6 extends from the distal end of the blade 3, that is the cutting point 4, to the corresponding proximal end 5 of the blade 3. The blade 3 includes the first side (the front side 7) and the second side (the rear side 8), each of which extends between the opposing outer end lines 6. The cutting edge 6a is formed at least one of the outer end lines 6. Each first cutting surface 9 including the corresponding cutting edge 6a is formed in the front side 7 of the blade 3. The first cutting surface 9 includes the outer cutting surface 16 and the inner cutting surface 17, which extend between and along the corresponding cutting edge 6a and the associated inner end line 15, which is opposed to the cutting edge 6a.

The cutting angle (the semi cutting angle β17) between each inner cutting surface 17 and the hypothetical plane P6, which extends between the outer end lines 6 of the blade 3, is larger than the cutting angle (the semi cutting angle α16) between each outer cutting surface 16 and the hypothetical plane P6.

This structure makes it possible to form each of the cutting edges 6a relatively sharp, thus improving the cutting performance of the medical knife. Further, even though the cutting edges 6a are relatively sharp, the thickness between the front side 7 and the rear side 8 is assured to be sufficiently large such that the strength of the blade 3 becomes relatively great.

(2) The adjacent outer cutting surface 16 and the inner cutting surface 17 define the recess 9a recessed with respect to the hypothetical plane P9, which connects the outer end of the outer cutting surface 16 (the cutting edge 6a) to the inner end of the inner cutting surface 17 (the boundary inner end line 15).

The recess 9a of the first cutting surface 9 reduces the contact area between the blade 3 and a target biological tissue. This seconds the resulting frictional resistance to cutting, thus improving the cutting performance of the medical knife.

(3) The front side 7 of the blade 3 includes the opposing first cutting surfaces 9 each having the cutting edge 6a and the first intermediate surface 10 extending between the first cutting surfaces 9. The distance corresponding to the cutting angle (the semi cutting angles α16, β17) between each of the first cutting surfaces 9 and the hypothetical plane P6 gradually increases from the corresponding cutting edge 6a to the first intermediate surface 10. The angle θ10 between the first intermediate surface 10, which extends between the inner end line 15, and the hypothetical plane P15, which extends perpendicular to the hypothetical plane P6 and includes the corresponding inner end line 15, is larger than the angle θ17 between the inner cutting surface 17 of each first cutting surface 9, extending from the first intermediate surface 10, and the hypothetical plane P15.

This structure makes it possible to form the cutting edges 6a relatively sharp, enhancing the cutting performance of the medical knife. Further, the thickness between the front side 7 and the rear side 8 is assured to be sufficiently large, such that the strength of the blade 3 becomes improved reliably.

(4) In each first cutting surface 9, the width W16 of the outer cutting surface 16 between the cutting edge 6a and inner cutting surface 17 gradually increases from the cutting point 4 to the corresponding proximal end 5 of the blade 3. In contrast, the width W17 of the inner cutting surface 17 between the outer cutting surface 16 and the first intermediate surface 10 gradually decreases from the distal end 13 to the proximal end 5 of the blade 3.

In each of the first cutting surfaces 9, in the vicinity of the cutting point 4 of the blade 3, the width W17 of the inner cutting surface 17 is larger than the width W16 of the outer cutting surface 16. This structure decreases resistance to cutting when the cutting point 4 is introduced into the target biological tissue. Further, the thickness between the front side 7 and the rear side 8 is assured to be sufficiently large, such that the strength of the blade 3 is improved. Accordingly, the strength of the cutting point 4 is increased in a manner comfortable to the operator.

(5) The first intermediate surface 10 defines the recess 10a, recessed with respect to the hypothetical plane P10 extending between the inner end lines 15, each of which is located between the first intermediate surface 10 and the corresponding first cutting surface 9. The recess 10a forms a continuous arched surface extending between and along the inner end lines 15. Each of the inner end lines 15 extends from the distal end 13 of the first intermediate surface 10 to the corresponding proximal end 14. The width L of the intermediate surface 10 gradually increases from the distal end 13 to the proximal end 14.

This structure decreases the contact area between the blade 3 and the target biological tissue, thus seconding the frictional resistance. Accordingly, the cutting performance of the medical knife is improved.

A medical knife according to a second embodiment of the present invention will be described with reference to FIGS. 5(a) to 7(d). The description will focus on the difference between the first embodiment and the second embodiment. In the second embodiment, the rear side 8 of the blade 3 is configured identically to the front side 7. Further, in each of the cutting surfaces 9 of the front side 7 and the rear side 8, the semi cutting angle $\beta 17$ of the inner cutting surface 17 is larger than the semi cutting angle $\alpha 16$ of the outer cutting surface 16. The full cutting angle (semi cutting angle $\beta 17$+semi cutting angle $\beta 17$) of the inner cutting surfaces 17 of the corresponding cutting surfaces 9 of the front side 7 and the rear side 8 is thus larger than the full cutting angle (semi cutting angle $\alpha 16$+semi cutting angle $\alpha 16$) of the outer cutting surfaces 16 of the corresponding cutting surfaces 9 of the front side 7 and the rear side 8.

A medical knife according to a third embodiment of the present invention will be described with reference to FIGS. 8(a) to 10(d). The description will focus on the difference between the first embodiment and the third embodiment. In the third embodiment, the outer cutting surface 16 of each first cutting surface 9 is configured differently than that of the first embodiment. That is, the outer cutting surface 16 of the third embodiment includes a pair of cutting surface sections 22, 23. The cutting surface section 22 includes the cutting edge 6a, while the cutting surface section 23 includes the concave line 18 between the outer cutting surface 16 and the inner cutting surface 17. A boundary line 24 is defined between the cutting surface sections 22, 23. In each first cutting surface 9, a semi cutting angle $\alpha 22$ is defined between the cutting surface section 22 of the outer cutting surface 16 and the hypothetical plane P6 extending between the cutting edges 6a. Likewise, a semi cutting angle $\alpha 23$ is defined between the cutting surface section 23 of the outer cutting surface 16 and the hypothetical plane P6. Further, the semi cutting angle $\beta 17$ between the inner cutting surface 17 of each of the first cutting surfaces 9 and the hypothetical plane P6 is larger than the semi cutting angles $\alpha 22$, $\alpha 23$ ($\alpha 23<\alpha 22$). As has been described, the semi cutting angle $\alpha 11$ is defined between each of the second cutting surfaces 11 and the hypothetical plane P6. A full cutting angle (semi cutting angle $\beta 17$+semi cutting angle $\alpha 11$) defined by each second cutting surface 11 and the inner cutting surface 17 of the corresponding first cutting surface 9 is larger than a full cutting angle (semi cutting angles $\alpha 22$, $\alpha 23$+semi cutting angles $\alpha 11$) defined by the outer cutting surface 16 of each first cutting surface 9 and the corresponding second cutting surface 11. The recessed amount H10 of the recess 10a with respect to the hypothetical plane P10 is constant from the distal end 13 of the inner end line 15 to each of the proximal ends 14.

Figure 11:
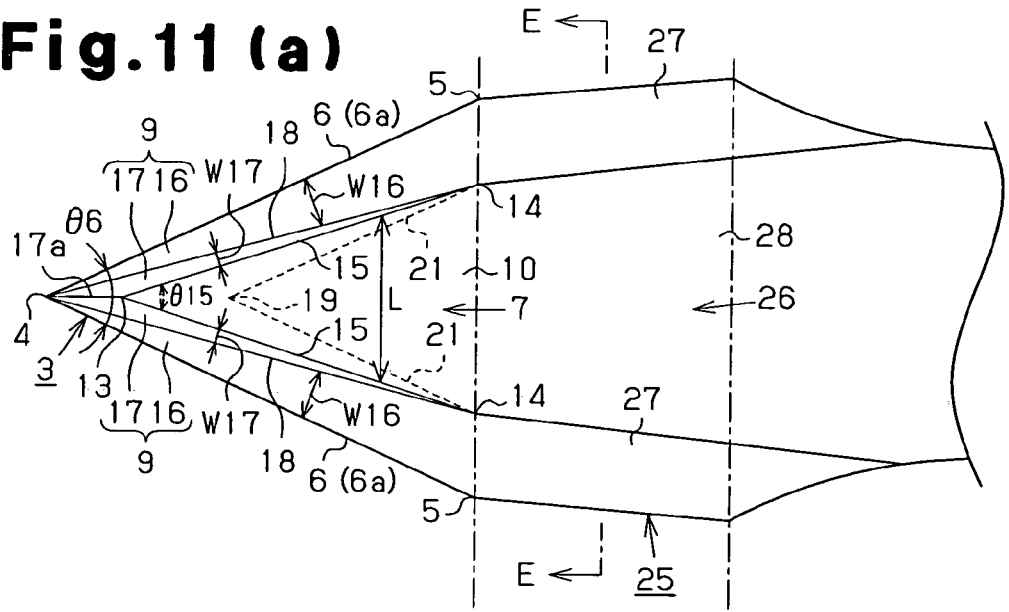
FIG. 11(a) is an enlarged view showing a portion of a front side of a blade according to a fourth embodiment of the present invention.
FIG. 11(b) is an enlarged view showing a portion of a rear side of the blade of FIG. 11(a)
FIG. 11(c) is an enlarged cross-sectional view taken along line E-E of FIG. 11(a)
Figure 11:
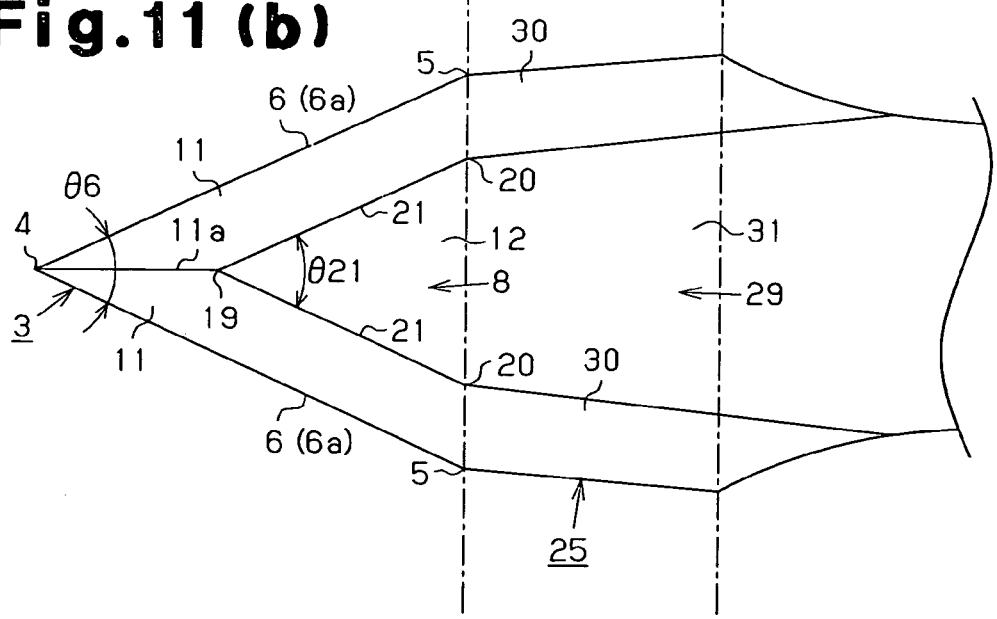
Figure 11:
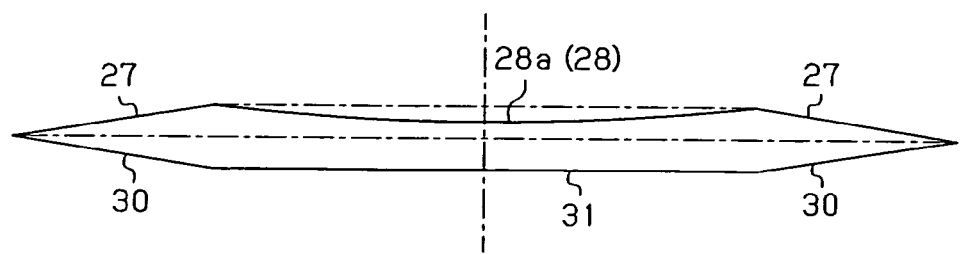

A medical knife according to a fourth embodiment of the present invention will be described with reference to FIGS. 11(a) to 11(c). The description will focus on the difference between the first embodiment and the fourth embodiment. In the fourth embodiment, a blade 25 is formed continuously from the blade 3. The blade 25 has a front side 26 including a pair of opposed cutting surfaces 27. Each of the cutting surfaces 27 is formed continuously from the outer cutting surface 16 of the corresponding first cutting surface 9 of the blade 3. An intermediate surface 28 extends between the cutting surfaces 27 and continuously from the first intermediate surface 10 of the blade 3. The intermediate surface 28 defines a recess 28a continuously from the recess 10a of the first intermediate surface 10 of the blade 3. The blade 25 further has a rear side 29 having a pair of opposed cutting surfaces 30. Each of the cutting surfaces 30 is formed continuously from the corresponding second cutting surface 11 of the blade 3. A planar intermediate surface 31 extends between the cutting surfaces 30 and continuously from the planar second intermediate surface 12 of the blade 3.

The present invention may be embodied in the following modifications.

In each of the first to fourth embodiments, laser marking may be performed on a front side of the plate 2 or a planar or curved surface of the handle 1 for indicating various types of product information such as cutting depth or cutting size or cutting direction of the blade 3, as well as specific type or use of the medical knife.

Figure 12A:
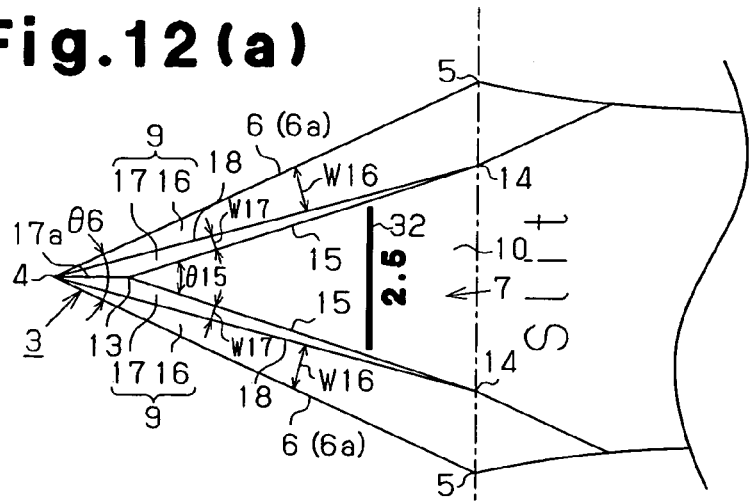
FIGS. 12(a) to 12(c) and 13(a) to 13(c) are views showing first to sixth modifications of the first embodiment, respectively.

For example, as a first modification of the first embodiment illustrated in FIG. 12(a), a marking line 32 is formed linearly along the width of the first intermediate surface 10. The width of the blade 3 at the marking line 32, that is, the dimension between the crossing point of the cutting edges 6a and a hypothetical line extending along the marking line 32 is 2.5 millimeters, as indicated in the drawing. The dimension corresponds to the cutting size. Further, the marked letters "Slit" indicate the specific type of the knife.

Figure 12B:
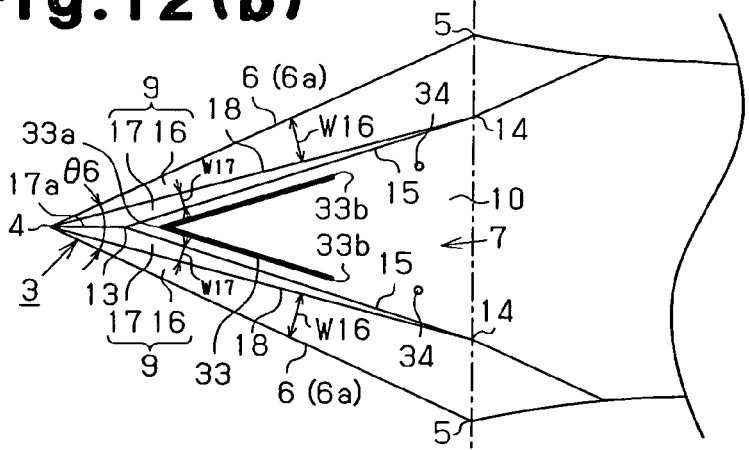

Alternatively, as a second modification of the first embodiment illustrated in FIG. 12(b), a V-shaped marking line 33 is formed along the inner end lines 15 in the first intermediate surface 10. Further, a pair of marking points 34 are provided in the vicinity of the proximal ends 14. In this case, the dimension between the crossing point of the cutting edges 6a and a hypothetical line including a point 33a or a pair of opposed ends 33b of the V-shaped marking line 33 or the marking points 34 and extending along the width of the first intermediate surface 10 corresponds to a cutting size, although the particular numbers are not specified.

Figure 12C:
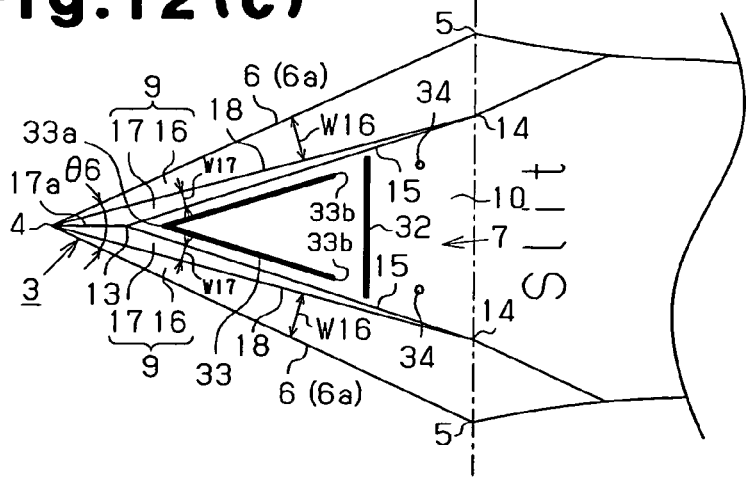

As a third modification of the first embodiment illustrated in FIG. 12(c), the aforementioned first and second modifications of the first embodiment are combined.

Figure 13A:
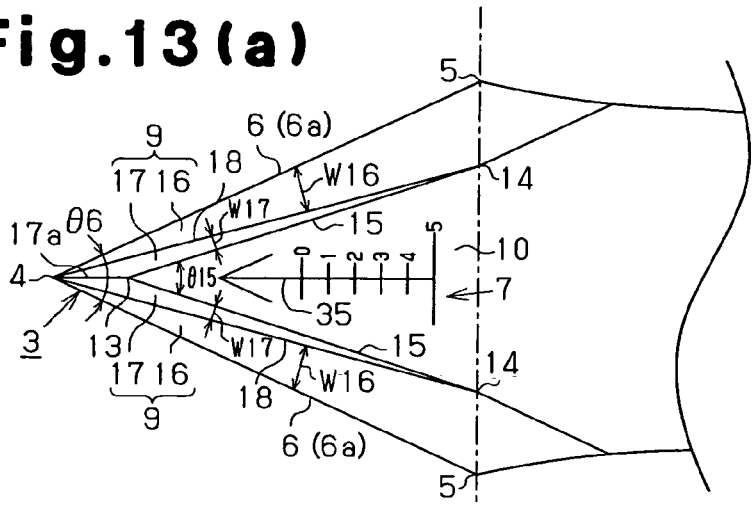

Further, as a fourth modification of the first embodiment illustrated in FIG. 13(a), an arrow-like marking line 35 is formed in the first intermediate surface 10 for indicating the cutting direction. Further, six levels from "0" to "5" are marked along the line 35. The dimension between the crossing point of the cutting edges 6a and a hypothetical line including the point of the arrow-like line 35 or each of the level markings and extending along the width of the first intermediate surface 10 corresponds to a cutting size, although the particular numbers are not specified.

Figure 13B:
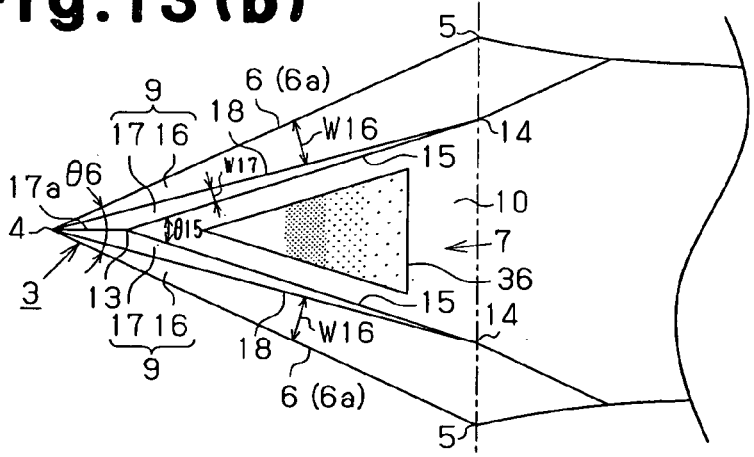

Alternatively, as a fifth modification of the first embodiment illustrated in FIG. 13(b), a triangular, shaded-color marking portion 36 is formed in the first intermediate surface 10. The marking portion 36 includes four gradually shaded color areas. The dimension between the crossing point of the cutting edges 6a and a hypothetical line including each of the four color areas and extending along the width of the first intermediate surface 10 corresponds to a cutting size, although the particular numbers are not specified.

Figure 13C:
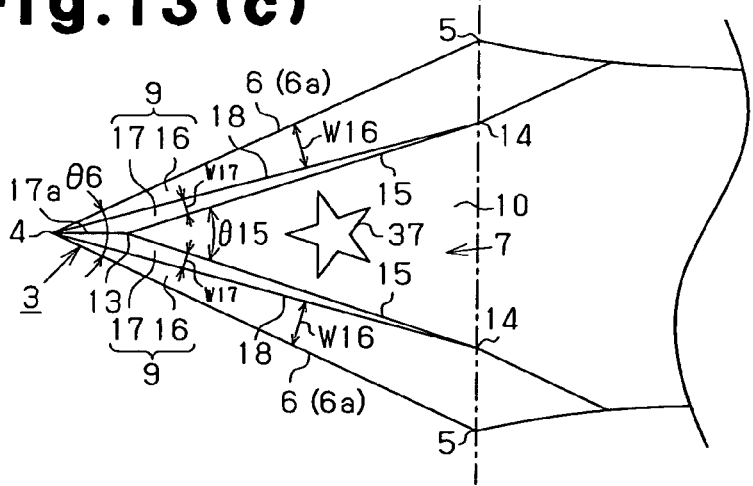
Figure 14:
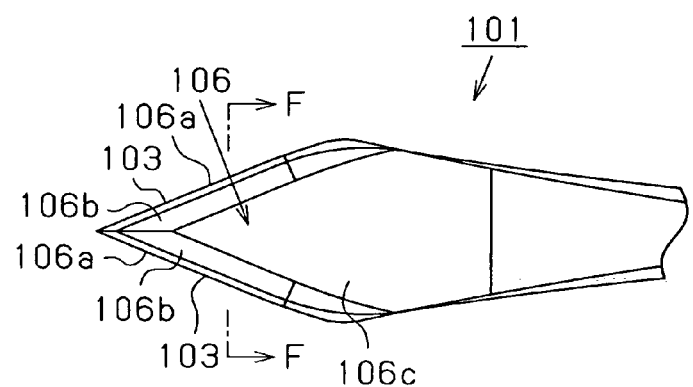
FIG. 14 is a front view showing a portion of a conventional medical knife.
Figure 15:
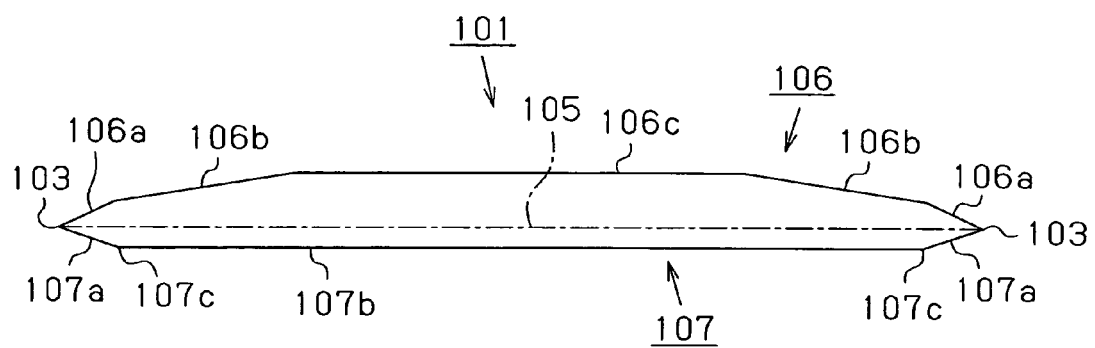
FIG. 15 is an enlarged cross-sectional view taken along line F-F of FIG. 14.

Also, as a sixth modification of the first embodiment indicated by FIG. 13(c), a star-shaped marking portion 37 is formed in the first intermediate surface 10. The dimension between a hypothetical line including each of the points of the marking portion 37 and extending along the width of the first intermediate surface 10 corresponds to a cutting size, although the particular numbers are not specified.

The present examples and embodiments are to be considered as illustrative and not restrictive and the invention is not to be limited to the details given herein, but may be modified within the scope and equivalence of the appended claims.

The invention claimed is:

1. A medical knife having a blade, the blade including:
a distal end and a proximal end;
a pair of opposed, first and second sides extending from the distal end to the proximal end;
a pair of cutting edges formed between the first and second sides and extending from the distal end to the proximal end;
a pair of boundary lines defined on the first side and extending from the distal end to the proximal end; and
a pair of cutting surfaces formed on the first side, each of the cutting surfaces being defined between one of the cutting edges and a corresponding one of the boundary lines,
wherein each of the cutting surfaces includes an outer cutting surface formed continuously with a corresponding one of the cutting edges and an inner cutting surface formed continuously with a corresponding one of the boundary lines, wherein an angle of each of the inner cutting surfaces with respect to a first hypothetical plane is larger than an angle of the outer cutting surfaces with respect to the first hypothetical plane, and wherein the first hypothetical plane includes the first and second sides,
wherein the inner cutting surfaces are connected to each other at a connecting portion in the vicinity of the distal end,
wherein a width of each of the outer cutting surfaces between a corresponding one of the cutting edges and the corresponding inner cutting surface is gradually increased from the distal end to the proximal end, and a width of each of the inner cutting surfaces between a corresponding one of the boundary lines and a corresponding one of the outer cutting surfaces is gradually decreased from the connecting portion to the proximal end, and
wherein an intermediate surface is formed on the first side between the inner cutting surfaces, the pair of boundary lines being located between the intermediate surface and the inner cutting surfaces, the intermediate surface having an arch-shaped recessed surface with respect to a second hypothetical plane, the second hypothetical plane including the pair of boundary lines.

2. The medical knife according to claim 1, wherein
said first hypothetical plane includes the cutting edges,
the angle of each of the inner cutting surfaces with respect to the first hypothetical plane is not smaller than 10 degrees but not larger than 60 degrees, and
the angle of each of the outer cutting surfaces with respect to the hypothetical plane is not smaller than 5 degrees but not larger than 30 degrees.

3. The medical knife according to claim 1, wherein:
the boundary lines and the cutting surfaces on the first side are a first pair of boundary lines and a first pair of cutting surfaces, respectively; and
the blade further includes a second pair of boundary lines defined on the second side and extending from the distal end to the proximal end, wherein a pair of sections of the second side between the cutting edges and the second boundary lines form a pair of second cutting surfaces, respectively, wherein an angle of a section of each of the second cutting surfaces in the vicinity of the second pair of boundary lines with respect to the hypothetical plane is larger than an angle of a section of each of the pair of second cutting surfaces in the vicinity of the cutting edges with respect to the hypothetical plane.

4. The medical knife according to claim 3, wherein
each of the second cutting surfaces includes at least an outer cutting surface formed continuously with a corresponding one of the cutting edges and an inner cutting surface formed continuously with a corresponding one of the boundary lines, and
wherein the angle of each of the inner cutting surfaces with respect to the hypothetical plane is larger than the angle of the outer cutting surfaces with respect to the hypothetical plane.

5. The medical knife according to claim 1, wherein:
the boundary lines and the cutting surfaces on the first side are a first pair of boundary lines and a first cutting pair of cutting surfaces, respectively; and
the blade further includes a second pair of boundary lines defined on the second side and extending from the distal end to the proximal end, wherein a pair of sections of the second side between the cutting edges and the second boundary lines form a pair of second cutting surfaces, and wherein an angle of each of a pair of sections of the second cutting surfaces with respect to the first hypothetical plane is constant between each of the boundary lines of the second pair of boundary lines and the corresponding one of the cutting edges.

6. The medical knife according to claim 1, wherein:
each of the cutting edges includes a first distal end corresponding to the distal end of the blade and a first proximal end corresponding to the proximal end of the blade, and each of the boundary lines includes a second distal end connected to the connecting portion and a proximal end located near the proximal end of the blade;
each of the outer cutting surfaces is contoured by a first line, a second line and a third line, wherein the first line interconnects the second proximal end to the first distal end, the second line interconnects the first distal end to the first proximal end, and the third line interconnects the first proximal end to the second proximal end, and
each of the inner cutting surfaces is contoured by the first line, the boundary line and a fourth line, wherein the fourth line interconnects the first distal end to the second distal end.

7. A medical knife having a blade, the blade including:
a distal end and a proximal end;

a pair of opposed, first and second sides extending from the distal end to the proximal end;

a pair of cutting edges being formed between the first and second sides and extending from the distal end to the proximal end;

a pair of boundary lines defined on the first side and extending from the distal end to the proximal end;

a pair of first cutting surfaces formed on the first side, each of the cutting surfaces being defined between one of the cutting edges and a corresponding one of the boundary lines; and a pair of second cutting surfaces formed on the second side corresponding to the first cutting surfaces, wherein each of the first cutting surfaces includes an outer cutting surface formed continuously with a corresponding one of the cutting edges and an inner cutting surface formed continuously with a corresponding one of the boundary lines, wherein the angle of each of the inner cutting surfaces with respect to a first hypothetical plane is larger than the angle of the outer cutting surfaces with respect to the first hypothetical plane, and wherein the first hypothetical plane includes the first and second sides, wherein the inner cutting surfaces are connected to each other at a connecting portion in the vicinity of the distal end, wherein a width of each of each of the outer cutting surfaces between a corresponding one of the cutting edges and a corresponding one of the inner cutting surfaces is gradually increased from the distal end to the proximal end, and a width of each of the inner cutting surfaces between a corresponding one of the boundary lines and a corresponding one of the outer cutting surfaces is gradually decreased from the connecting portion to the proximal end, and wherein an intermediate surface is formed on the first side between the inner cutting surfaces, the pair of boundary lines is located between the intermediate surface and the inner cutting surfaces, the intermediate surface has a recessed surface with respect to a second hypothetical plane, and the second hypothetical plane includes the pair of boundary lines.

8. The medical knife according to claim 1, wherein the ratio of the recessed amount of the arch-shaped recessed surface with respect to the second hypothetical plane to a maximum value of the thickness of the blade is not smaller than 0.05 but not larger than 0.5.

9. The medical knife according to claim 1, wherein the recessed amount of the arch-shaped recessed surface with respect to the second hypothetical plane is not smaller than 0.05 millimeters but not larger than 0.5 millimeters.

10. The medical knife according to claim 1, each of the cutting surfaces corresponding to a first cutting surface, the intermediate surface corresponding to a first intermediate surface, the blade further including:

a pair of second cutting surfaces formed on the second side, each of the second cutting surfaces being connected to a corresponding one of the cutting edges; and a second intermediate surface formed on the second side between the second cutting surfaces, the second intermediate surface being a plane extending between a second pair of boundary lines between the second intermediate surface and the second cutting surfaces.

11. The medical knife according to claim 1, wherein the pair of cutting surfaces is a first pair of cutting surfaces that formed on the first side, the intermediate surface corresponds to a first intermediate surface, and the blade further includes:

a second pair of cutting surfaces formed on the second side, each of the second pair of cutting surfaces being connected to a corresponding one of the cutting edges; and a second intermediate surface is formed on the second side between the second pair of cutting surfaces, the second intermediate surface having a recessed surface with respect to a hypothetical plane extending between a pair of boundary lines, which are between the second intermediate surface and the second cutting surfaces.

12. The medical knife according to claim 1, wherein the first hypothetical plane extends between the cutting edges, wherein the angle of the inner cutting surfaces with respect to the first hypothetical plane is not smaller than 20 degrees but not larger than 40 degrees, and wherein the angle of the outer cutting surfaces with respect to the first hypothetical plane is not smaller than 5 degrees but not larger than 30 degrees.

* * * * *